United States Patent [19]

Sarian

[11] 4,088,953
[45] May 9, 1978

[54] EDDY-CURRENT TEST PROBE UTILIZING A COMBINATION OF HIGH AND LOW RELUCTANCE MATERIALS TO OPTIMIZE PROBE SENSITIVITY

[75] Inventor: Suren Sarian, Seattle, Wash.

[73] Assignee: The Reluxtrol Company, San Mateo, Calif.

[21] Appl. No.: 741,666

[22] Filed: Nov. 15, 1976

Related U.S. Application Data

[63] Continuation-in-part of Ser. No. 538,955, Jan. 6, 1975, abandoned.

[51] Int. Cl.² ................................... G01R 33/12
[52] U.S. Cl. ........................... 324/232; 324/238; 336/84 R; 336/178; 336/212
[58] Field of Search ............ 324/34 R, 34 TK, 34 D, 324/34 PS, 40; 336/84, 212, 83, 178; 360/119, 120, 121, 128, 129

[56] References Cited

U.S. PATENT DOCUMENTS

| 2,162,710 | 6/1939 | Gunn | 324/37 |
|---|---|---|---|
| 2,526,977 | 10/1950 | Smith | 336/84 X |
| 2,555,110 | 5/1951 | Bobb | 360/119 |
| 2,852,618 | 9/1958 | Hansen | 360/120 |
| 2,933,677 | 4/1960 | Lieber | 324/34 |
| 2,998,583 | 8/1961 | Worcester | 336/232 X |
| 3,017,485 | 1/1962 | Hansen | 336/84 X |
| 3,197,693 | 7/1965 | Libby | 324/40 |
| 3,312,919 | 4/1967 | Ross | 336/84 C |
| 3,378,626 | 4/1968 | Tucker | 336/84 X |
| 3,526,725 | 9/1970 | Camnas | 360/120 X |
| 3,534,177 | 10/1970 | Camnas | 360/121 |
| 3,626,344 | 12/1971 | Shaternikov | 336/73 |
| 3,792,396 | 2/1974 | Pann | 336/178 X |
| 3,840,802 | 10/1974 | Anthony | 336/84 X |

OTHER PUBLICATIONS

Pasley et al., Eddy Current Testing, Nondestructive Testing, NASA, 1963, 620, 1127, 5089N, pp. 101–118.

Primary Examiner—Robert J. Corcoran
Attorney, Agent, or Firm—Graybeal, Barnard & Uhlir

[57] ABSTRACT

A coil of insulated wire surrounds a low reluctance core. A combination of low reluctance and high reluctance materials positioned adjacent said coil: (1) control the spatial extent of the magnetic flux and, (2) concentrate the total reluctance of the magnetic circuit of the exciting coil into a volume of controlled size and shape within the material being tested. The magnetic flux is controlled, and the reluctance is concentrated, in such a manner as to optimize the sensitivity of the eddy-current generator to variations in the material being tested; at the same time, the coil impedance is maintained at a value which is optimum for the performance of any selected precision electrical impedance measuring device.

13 Claims, 13 Drawing Figures

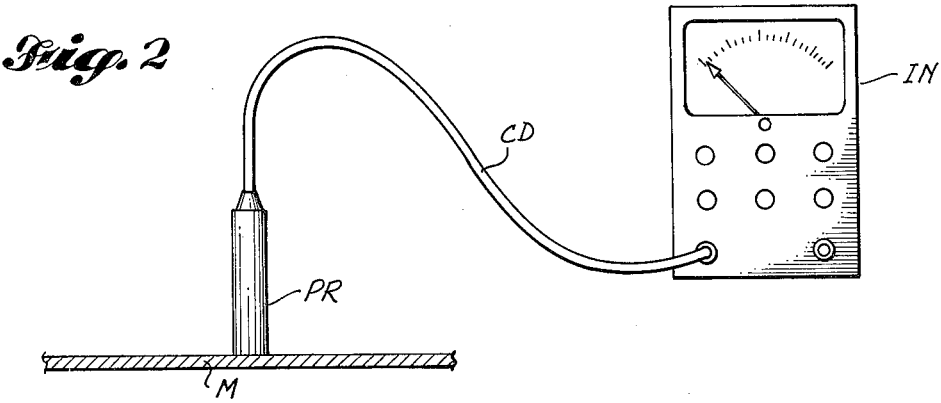
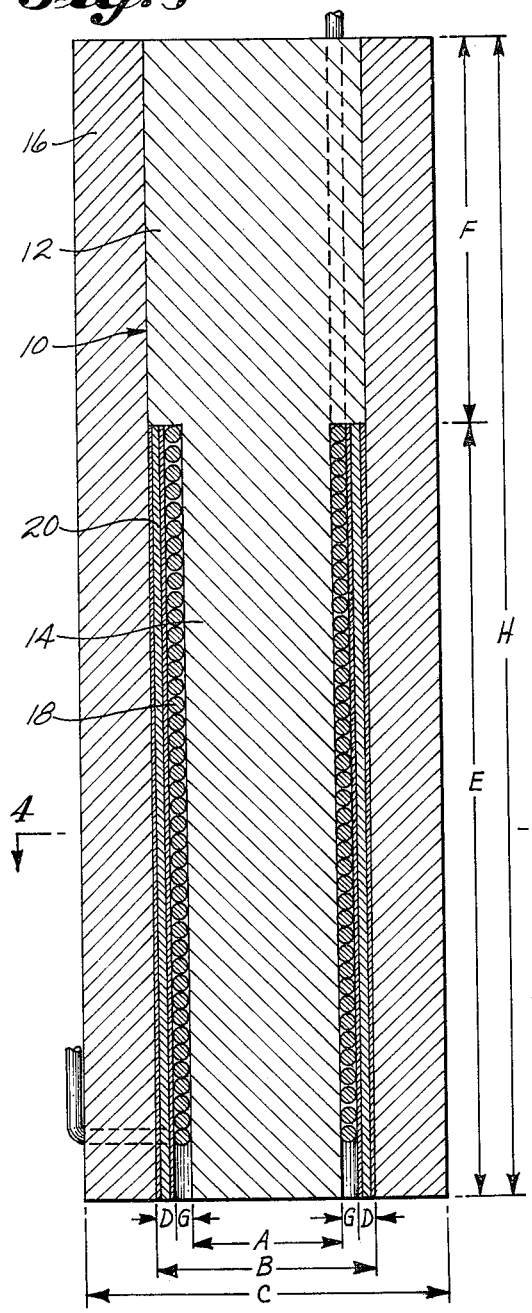
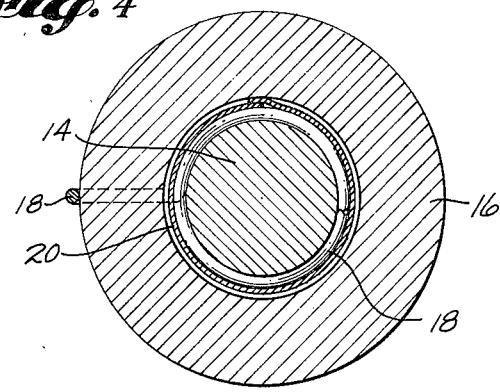
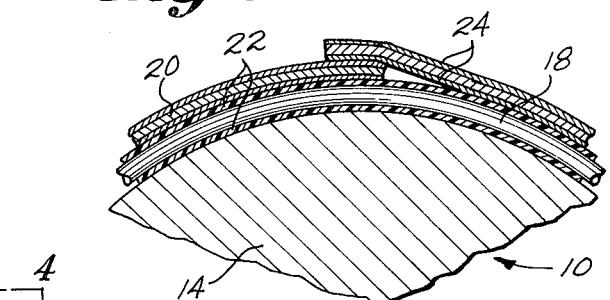
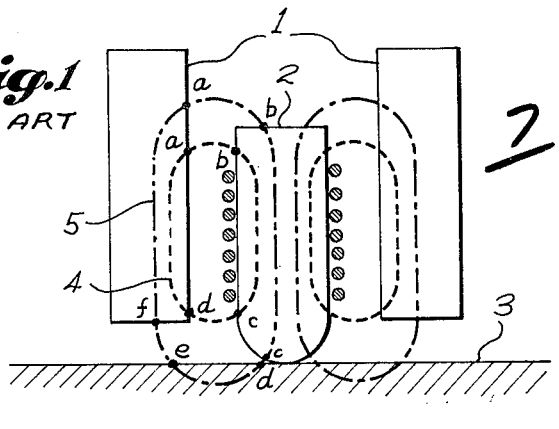

EDDY-CURRENT TEST PROBE UTILIZING A COMBINATION OF HIGH AND LOW RELUCTANCE MATERIALS TO OPTIMIZE PROBE SENSITIVITY

CROSS-REFERENCE TO RELATED APPLICATION

This is a continuation-in-part of my prior, now abandoned application Ser. No. 538,955, filed Jan. 6, 1975, and also entitled Eddy-Current Flux Generator for Testing of Materials.

BACKGROUND OF THE INVENTION

Field of the Invention

The present invention relates to eddy-current testing, and more particularly to improved eddy-current generators characterized by a significantly greater sensitivity to near-surface imperfections, greater inspection sweep-widths, and smaller sensitivity to edge effects, in comparison with known eddy-current generators.

General Discussion of Eddy-Current Testing

Eddy-current inspection is a method of locating surface or subsurface flaws in electrically conductive materials, or evaluating such material characteristics as hardness, thickness, heat-treatment condition, and/or other metallurgical conditions. The test article is brought into a time-varying electromagnetic field that produces electric currents. Typical currents of this sort resemble in form the eddies in flow streams of turbulent water; hence, they are called eddy-currents. The amount of electrical current flowing in these eddies is determined by the electrical conductivity and magnetic permeability of the test object as well as the frequency and amplitude of the applied electromagnetic field. These eddy-currents in turn create their own electromagnetic field, which may be sensed either through its effect upon the impedance of the primary excitation coil, or through its effect upon the pick-up of an independent sensing coil.

The basic element in any eddy-current materials testing apparatus is an eddy-current generator positionable adjacent to the surface of the material to be evaluated.

The applications of eddy-current testing include:

1. Flaw detection and measurement in the near-surface regions of ferrous and non-ferrous metals and alloys.
2. Detection and measurement of fatigue damage in the near-surface regions of ferrous and non-ferrous metals and alloys.
3. Detection and measurement of oxidation and corrosion of metals and alloys.
4. Measurement of the thickness of electrically non-conducting coatings on metals and alloys.
5. Measurement of the thickness of electrically conducting coatings on non-conducting substrates.
6. Measurement of the near-surface hardness of thermally treated metals and alloys (case-hardening, for example).
7. Measurement of the near-surface properties (hardness, for example) of thermochemically treated (carburized, decarburized, nitrided) steels, and other metals and alloys.
8. Measurement of the amount of cold-working in metals and alloys.
9. Detection and measurement of surface stresses and strains.
10. Indirect measurement of physical properties by measuring the near-surface susceptibility and near-surface conductivity.
11. Measurement of the thickness of nickel and/or chromium plating on carbon steels.
12. Detection of flaws and porosity in brazed, welded, or solder joints.
13. Porosity detection and measurement in ferrous and non-ferrous metals and alloys.
14. Measurement of the thickness of ferrous and non-ferrous alloy sheet and tubing.
15. Measurement of the eccentricity and wall thickness uniformity of ferrous and non-ferrous metal and alloy tubing.
16. Detection of metallic inclusions in insulators and semi-conductors.
17. Detection of non-conducting inclusions and precipitate particles in metals and alloys.
18. Measurement of surface temperatures.

General Discussion of the Invention and Discussion of the Prior Art

The present invention relates to the provisions of eddy-current generators which are sensitive to relatively small variations in near-surface conditions. The near-surface conditions are monitored by sensing the effect of the eddy-currents on the impedance of the excitation coil. The greater sensitivity to the condition being measured is achieved by controlling the spatial extent of the magnetic flux and by concentrating the magnetic reluctance of the eddy-current generator into a volume of controlled size and shape in the sub-surface of the material being evaluated.

This flux and reluctance control allows the design of eddy-current generators with significantly greater sensitivity to near-surface conditions, greater inspection sweep-widths, and smaller sensitivity to perturbing edge effects than is possible with conventional eddy-current generators. This can be accomplished while maintaining the electrical impedance of the eddy-current generator at a value which is near the optimum for the performance of any selected precision electrical impedance measuring device.

The eddy-current generators of interest herein comprise a single coil of electrically conductive wire and the electrical impedance Z of this coil is monitored as the eddy-current generator is moved relatively along the surface of the material being evaluated. Variations in Z are a measure of variations within the near-surface regions of the material being evaluated.

Neglecting the resistance of the wire and stray capacitance, the impedance of the coil is given by $Z = iwL$, where the inductance $L = N^2/R$, $w$ is the frequency of the electromagnetic signal, N is the number of turns of wire comprising the coil, R is the magnetic reluctance of the coil, and $i$ is the quantity $(-1)^{\frac{1}{2}}$.

One may divide the reluctance of the magnetic circuit of the coil into two parallel contributions. One contribution $R_p$, which herein shall be referred to as the parallel reluctance, affects the flux which does not pass through the material being evaluated and the second contribution affects the flux which does pass through the material being evaluated. This second reluctance is in turn made up of two series contributions. One is the reluctance experienced by the flux when it is outside of the material being evaluated, which herein shall be referred to as the series reluctance $R_s$, and the second is $R_m$, the reluctance experienced by the flux when it is inside the material being evaluated. Here $R_m$ will be complex and it will be frequency dependent because of the eddy-current contribution. The following equivalent magnetic circuit illustrates the inter-relationship between the various reluctances.

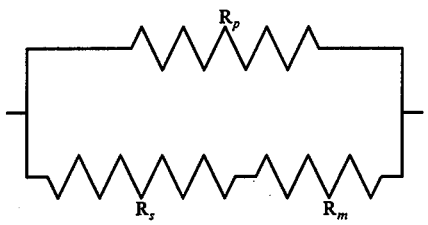

The inductance of the coil is then given approximately by $L = N^2(R_p+R_s+R_m)(R_s+R_m)^{-1}R_p^{-1}$. The fractional change in inductance $$\Delta L/L = -R_p(R_s+R_m)^{-1}(R_p+R_s+R_m)^{-1}\Delta R_m \quad (1)$$

is a measure of the sensitivity of the eddy-current generators to material variations.

It is evident from Equation (1) that the maximum sensitivity is obtained if $R_p >> R_m >> R_s$; that is, if the total reluctance of the magnetic circuit of the coil is concentrated in the material being evaluated. For $R_p >> R_m >> R_s$, $$L \doteq N^2/R_m, \quad (2a)$$

and $$\Delta L/L \doteq -\Delta R_m/R_m \quad (2b)$$

For a material containing a small defect, the material reluctance $R_m$ can be divided into two parallel contributions. One contribution $R_d$ controls the flux which passes through the defect volume. The second contribution $R_m^*$ controls the flux which does not pass through the defect volume. The equivalent magnetic circuit for the material reluctance is illustrated by the following diagram

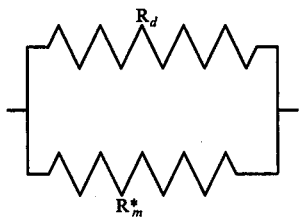

and the material reluctance can be approximated by the following Equation (3):

$$R_m \doteq R_m^* R_d(R_m^* + R_d)^{-1}. \quad (3)$$

Here, we mean by a small defect that the flux flowing through the defect volume will be much less than the total flux flowing through the material. Here, $R_d >> R_m^*$ and $R_m \doteq R_m^*$. The change in material reluctance resulting from a small material defect is then given by $$\Delta R_m = (R_m/R_d)^2 \Delta R_d, \quad (4)$$

where $\Delta R_d$ is the difference in $R_d$ for a defect-free material and one containing a defect. If we optimize the sensitivity to small defects by making $R_p >> R_m >> R_s$ then $$\Delta L/L = (R_m/R_d)(\Delta R_d/R_d). \quad (5)$$

$R_m$ is proportional to $p^2/v$ and $R_d$ is proportional to $p$, where $p$ is the effective flux path-length in the material being evaluated and $v$ is the effective volume of material being evaluated through which the flux passes. It follows from Equation (5) that $\Delta L/L$ is proportional to $v^{-1}$, that is, the sensitivity is inversely proportional to what herein shall be referred to as the reluctance volume.

In addition, the impedance measuring device places constraints on the optimum of L and correspondingly on $R_m$ [see Equation (2b)]. Hence for optimum sensitivity, one must minimize the reluctance volume while keeping the ratio $p^2/v$ equal to a constant. This means that significant advantages result from controlling the shape as well as the size of the reluctance volume.

A second advantage which results from control of the shape of the reluctance volume is that it allows the design of eddy-current generators with significantly greater sweep widths than are obtainable with conventional generators. A greater sweep path width means a greater area of the material surface can be probed in a single sweep.

In order to effectively concentrate the magnetic reluctance of the eddy-current generator into a small volume of controlled shape in the subsurface of the material to be investigated, it is necessary to make use of materials with low reluctance and materials with high reluctance in the construction of the eddy-current generator.

Many eddy-current generators use low reluctance materials which reduce, or in some cases essentially eliminate, $R_s$. However, in doing this, the low reluctance materials also decrease $R_p$ and in some cases this decrease in $R_p$ can result in a decreased coil sensitivity. U.S. Pat. No. 2,933,677, hereinafter discussed in some detail, is an example of an eddy-current generator constructed by using only low reluctance materials. Such eddy-current generators have not been successful in concentrating the reluctance in the material to be investigated nor in controlling the shape of the reluctance volume.

High a.c. reluctance, which is essential for concentrating and controlling the size and shape of the reluctance volume, can be obtained by using materials which have an electromagnetic skin depth which is much less than the distance which a typical flux line travels through that (high reluctance) material. Such materials have occasionally been used for shielding in eddy-current generators. The purpose of this shielding is to reduce the sensitivity of the eddy-current generator to nearby structural discontinuities such as edges and also to decrease the influence of external electromagnetic noise. Such an application is discussed in U.S. Pat. No. 3,626,344 which is also hereinafter discussed in some detail. In shielding applications, the high reluctance material reduces the reluctance volume which tends to increase the defect sensitivity of the coil, but it also increases $R_s$ which tends to reduce the defect sensitivity; thus, only marginal gains in defect sensitivity, as defined herein, have been obtained by such shielding.

Heretofore, high reluctance materials have not been used to concentrate the reluctance of the exciting coil within the material to be evaluated, nor to greatly affect $R_p$.

The general principles of eddy-current testing are discussed in such texts as "Nondestructive Testing," N.A.S.A., 1963, at pages 101–118; "Nondestructive Testing," by McGonnogle, at pages 346–390 and "Nondestructive Testing Handbook," by McMaster, at pages 36.1 – 36.21.

Known United States patents which should be considered for background purposes are: U.S. Pat. No. 2,933,677, granted Apr. 19, 1960 to Sidney V. Lieber and U.S. Pat. No. 3,626,344, granted Dec. 7, 1971 to Viktor E. Shaternikov and Vladen A. Denisov.

U.S. Pat. No. 2,933,677 discloses an eddy-current generator comprising a single layered coil, a low reluctance magnetic material core for said coil, and a low reluctance magnetic material shield surrounding said coil for eliminating stray-field effects and for concentrating the effective measuring area of the probe. Such probe does not use high reluctance materials in its construction. Therefore, in most applications, the invention described in U.S. Pat. No. 2,933,677 cannot achieve the sensitivity to near-surface material variations possible with the invention described herein.

FIG. 1 of the drawing is a schematic illustration of the features which control the sensitivity of the probe disclosed by U.S. Pat. No. 2,933,677.

Referring to FIG. 1 of U.S. Pat. No. 2,933,677, the ferrite cylinder 1 and the inner core 2 are constructed of low reluctance materials. The reluctance of the material being tested 3 is generally larger than the reluctance of air. A typical flux line which does not pass through the material being tested, and hereinafter referred to as a parallel flux line, is illustrated by 4 and a typical flux line which does pass through the material being tested is illustrated by 5.

The magnitude of the flux line is controlled by the reluctance which it experiences as it passes through the various materials which comprise the loop. In sections 4da and 4bc of the loops, flux 4 passes through the low reluctance ferrite materials which present essentially zero reluctance to the flux. However, in sections 4ab and 4cd, the flux passes through air which controls the total reluctance experienced by the parallel flux. If $R_o$ is taken to be the reluctance of the material comprising section 4ab, as well as in section 4cd, then the total reluctance experienced by the parallel flux is given by the equation: $R_p \doteq 2R_o$.

The series reluctance, discussed previously, is given by the sum of the reluctance experienced by the flux path 5 passing through sections ef, fa, ab, bc, and cd. In sections 5fa and 5bc the flux passes through the ferrite material, hence the reluctance experienced by the flux in these sections is essentially zero. In section 5ab the reluctance is approximately $3R_o$ because the flux path length in this section is approximately 3 times the flux path length in section 4ab. In sections 5cd and 5ef the reluctance sum is approximately $R_o$. Hence $R_s \doteq 4R_o$.

The material reluctance, $R_m$, typically will be 10 to 20 times $R_o$. Therefore, from Equation (1), the sensitivity, $\Delta L/L$, of this construction is:

$$\frac{\Delta L}{L} = -\frac{2R_O}{(24R_O)(26R_O)} \cdot \Delta R_m \approx -0.003 \frac{\Delta R_m}{R_O}.$$

In contrast, in an embodiment of the subject invention, a high reluctance material is positioned in such a manner that sections 4ab and 4cd of the flux pass through the high reluctance material (for which typically, $R_p \doteq 200R_o$). In addition, the ferrite material is designed in such a manner that the geometrical path length of sections 5ab, 5cd and 5ef are very nearly zero; hence, we can assign as an upper limit: $R_s = 0.01R_o$. Again, taking $R_m = 20R_o$ and using Equation (1), the sensitivity of this construction is:

$$\frac{\Delta L}{L} \doteq -\frac{200 R_0}{(20R_O)(220R_O)} \cdot \Delta R_m \doteq -0.045 \frac{\Delta R_m}{R_O}.$$

Hence, by using a combination of high and low reluctance materials to concentrate the reluctance in the material being tested (i.e. by making $R_p >> R_m >> R_s$) the sensitivity of probes constructed in accordance with the present invention could be 15 times greater than a probe having the same construction as described in U.S. Pat. No. 2,933,677. Furthermore, because the combined use of both high and low reluctance materials makes it possible to control the shape of the reluctance volume, even greater sensitivity can be attained with the present invention by altering the geometric configuration of the reluctance volume as discussed on page 7, paragraph 3.

U.S. Pat. No. 3,626,344 discloses an eddy-current generator comprising an inductance coil provided with a ferrite core featuring at least one gap wherein an electromagnetic stray flux is created which interacts with the article being tested. A high conductivity non-magnetic plug is fixed in position within said gap, with the result that "there occur eddy-currents which expel the magnetic field out of the slot and create a stray field featuring sharp directivity and substantially higher intensity as compared with the heretofore known transducers." Copper and silver are listed as examples of the plug material.

A probe in accordance with the present invention differs from the probe disclosed by U.S. Pat. No. 3,626,344 in that it does not use a high conducting non-magnetic material to achieve substantially sharper directivity nor to achieve substantially higher flux intensities. Probes according to the present invention use a high reluctance material in the gap to eliminate the contribution of the parallel reluctance to the reluctance of the exciting coil. In probes embodying the present invention, the high reluctance material does not produce a substantial increase in the "stray" flux intensity nor does it produce substantially "sharper directivity" than is achieved without the high reluctance material. In addition, the sensitivity of probes embodying the present invention would be substantially worsened by the addition of a second gap described in connection with the claims and exemplary embodiment of U.S. Pat. No. 3,626,344.

Summary of the Invention

Eddy-current generators of the invention described herein are essentially characterized by:

a. low reluctance materials such as manganese-zinc ferrite constructed in such a manner as to essentially eliminate $R_s$, the series contribution to the reluctance of the excitation coil of the eddy-current generator; and other high permeability material may be used provided that the electromagnetic skin depth at the frequency of operation is much larger than the flux path length through the low reluctance material.

b. high reluctance materials such as Ni25Fe alloy or copper constructed in such a manner as to essentially eliminate $R_p$, the parallel reluctance contribution to the reluctance of the excitation coil of the eddy-current generator; any othermaterial may be used provided that the electromagnetic skin-depth at the frequency of operation is much less than the flux path length through the high reluctance material.

c. an excitation coil of insulated copper wire which is wound on the low reluctance ferrite core; any other wire may be used provided that the resistive contribution to the coil impedance due to the wire material is small compared to the inductive impedance of the coil.

d. a ferrite shape and number of coil turns, both of which are designed to achieve the desired sensitivity, sweep width, and inductance.

The unique features of such generators are:

1. The use of a combination of high and low reluctance materials to concentrate the reluctance of the eddy-current generator in the near-surface region of the material being evaluated.

2. The use of a combination of high and low reluctance materials to control the size and shape of the effective reluctance volume in order to achieve the desired sensitivity, sweep width, and inductance.

3. The use of high reluctance materials to significantly reduce the effect of the parallel reluctance of the eddy-current generators.

Glossary of Terms and Symbols

Electromagnetic skin depth: a characteristic parameter of the material since, at any given frequency of operation, it depends only on the conductivity and permeability of that material.

High Reluctance Material: a material which has an electromagnetic skin depth which is much less than the effective flux path length through that material.

Low Reluctance Material: a material with high permeability and an electromagnetic skin depth which is much greater than the effective flux path length through that material.

Parallel Reluctance, $R_p$: the effective reluctance which controls the flux which does not pass through the material being evaluated.

Series Reluctance, $R_s$: the effective reluctance experienced by the flux while it is outside the material being evaluated but which eventually does pass through the material being evaluated.

Material Reluctance, $R_m$: the effective reluctance experienced by the flux while it passes through the material being evaluated.

Defect Contribution to the Material Reluctance, $R_d$: the effective reluctance experienced by the flux while in the material being evaluated and which pass through the defect volume.

$R_m^*$: the effective reluctance experienced by the flux lines while in the material being evaluated but which pass outside of the defect volume itself.

$\Delta R_d$: the difference in $R_d$ between a defect-free material and one containing a defect.

Reluctance volume: the effective volume of the material being evaluated which has flux passing through it at any given time.

BRIEF DESCRIPTION OF THE DRAWING

In the drawing like letters and numerals refer to like parts, and:

FIG. 1 is a schematic illustration of the features which control the sensitivity of the probe disclosed by U.S. Pat. No. 2,933,677;

FIG. 2 is a view of a probe of the present invention in contact with a piece of material being tested;

FIG. 3 is a longitudinal sectional view of a first embodiment of the invention;

FIG. 4 is a cross-sectional view taken substantially along line 4—4 of FIG. 1;

FIG. 5 is an enlarged scale perspective view of an overlap region of the high reluctance material;

DESCRIPTION OF THE PREFERRED EMBODIMENTS

Referring to FIG. 2, a testing probe PR is shown in contact with a member M to be tested. Probe PR is connected by a flexible cord CR to an energizing and indicating unit IN, which may be of conventional construction and forms no part of this invention.

Figures 12, 13:
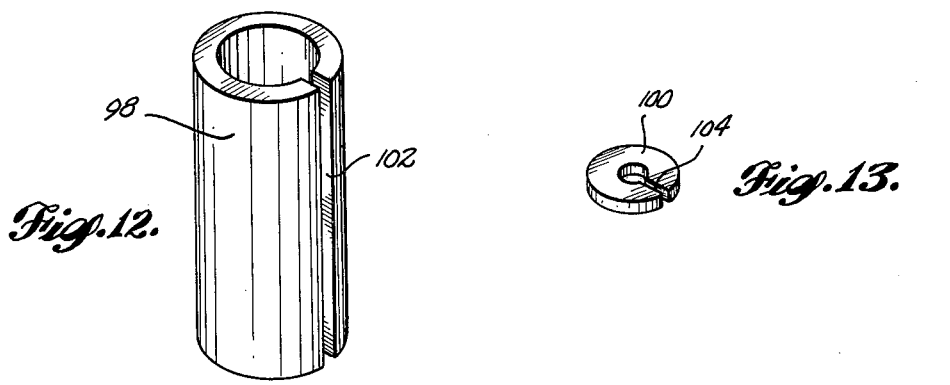
FIG. 12 is a reduced scale pictorial view of a sleeve of high reluctance material utilized in the embodiments of FIGS. 10 and 11.
FIG. 13 is also a reduced scale pictorial view, of a gap section portion of the high reluctance material utilized in the embodiments of FIGS. 10 and 11.

Referring to FIGS. 3 – 6, the first embodiment of the probe PR comprises an inner core 10 made from a low reluctance ferrite material. Core 10 includes a large diameter upper (as pictured) portion 12 and a considerably longer reduced diameter lower (as pictured) portion 14. Core 10 is received within an annular housing 16 which is also constructed from a low reluctance material, e.g. a ferrite material. Housing 16 is shown to have a constant dimension inner diameter which substantially equals the diameter of core portion 12. An annular space exists between the core part 14 and the outer housing 16. This space houses a coil 18 which is wrapped upon core part 14. A split annular sheet 20 of a high reluctance material surrounds coil 18 and substantially fills the space between coil 18 and outer housing 16. Coil 18 is preferably made from copper having an insulative coating 22 (FIG. 5). High reluctance material 20 may be made, for example, from Ni25Fe alloy, copper, silver or a mechanical combination of these materials. The split annular shape is made by wrapping around a mandrel, sheet which has been treated in such a manner that it is enveloped by an electrically non-conducting surface layer 24 (FIG. 5) or interrupted by a gap (FIG. 12).

For example, the Ni25Fe alloy may be heated over a flame prior to forming it on the mandrel. This would put an oxide layer on both surfaces which would serve as an electrically insulative coating.

According to the invention, an interruption is provided between the opposite ends of the sheet where they meet and such interruption is insulated so that current flow is arrested at the interruption. In the embodiment of FIGS. 3 – 6, a slight overlap is provided where the two ends of the sheet material meet. The insulative coating on the sheet material prevents current flow at the overlap. Alternatively, a gap could be maintained between the two ends of the sheet material to prevent circumferential current flow in the sheet material.

Figure 6:
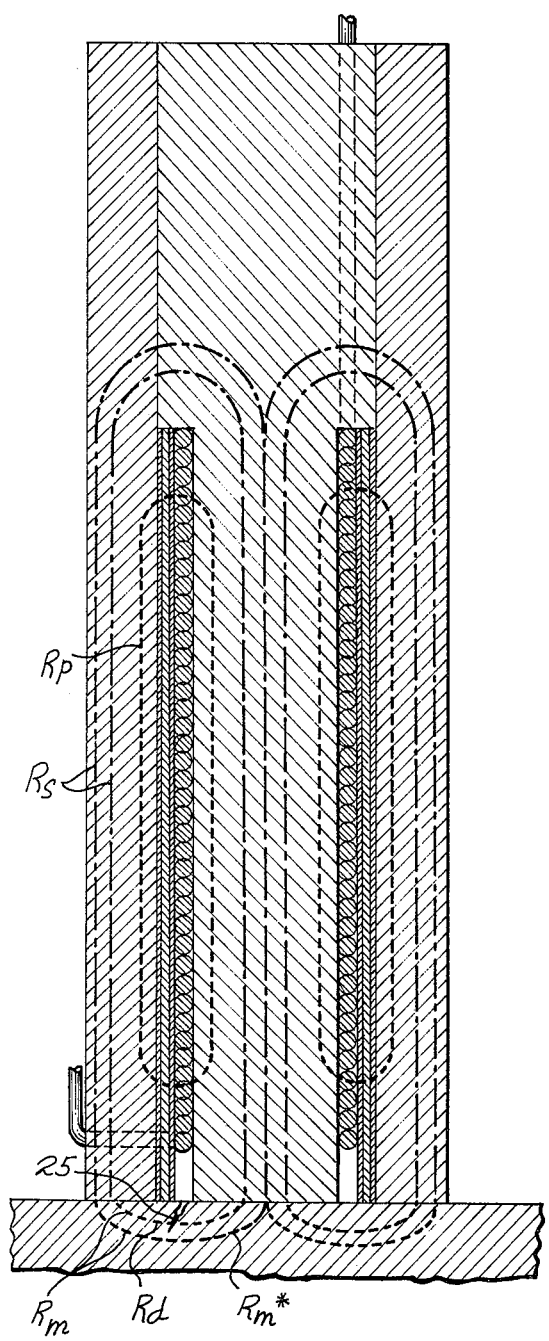
FIG. 6 is a view similar to FIG. 3, but showing the probe in close proximity with a surface to be tested; included in the figure are typical flux lines and associated reluctances.

Referring now to FIG. 6, this figure diagrammatically shows the effect of the construction of the present invention on the reluctances. With reference to such figure, the reluctances are defined in the Glossary of Terms and Symbols. The defect is designated 25.

$R_s$ and $R_m$ are in series and both are in parallel with $R_p$. $R_m$ is composed of $R_m^*$ and $R_d$ which are in parallel. Because of the positioning of the high reluctance material, the parallel flux is essentially zero in this designated construction.

For further clarification of the inter-relationship between the pertinent reluctances, the following diagram illustrates an equivalent circuit.

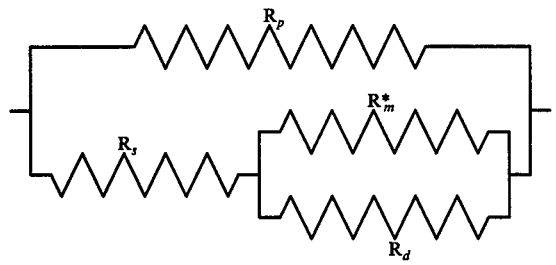

By way of typical and therefore non-limitative example of the cylindrical probe illustrated in FIGS. 3 – 6, the actual dimensions of such probes which have been successfully constructed and used are:

| | |
|---|---|
| A | 0.020" diam. |
| B | 0.029" – 0.035" diam. |
| C | 0.48" diam. |
| D | 0.005" – 0.002" thick annular sheet |
| E | 0.100" |
| F | 0.050" |
| G | 0.002" – 0.004" |
| H | 0.150" |

Figure 7:
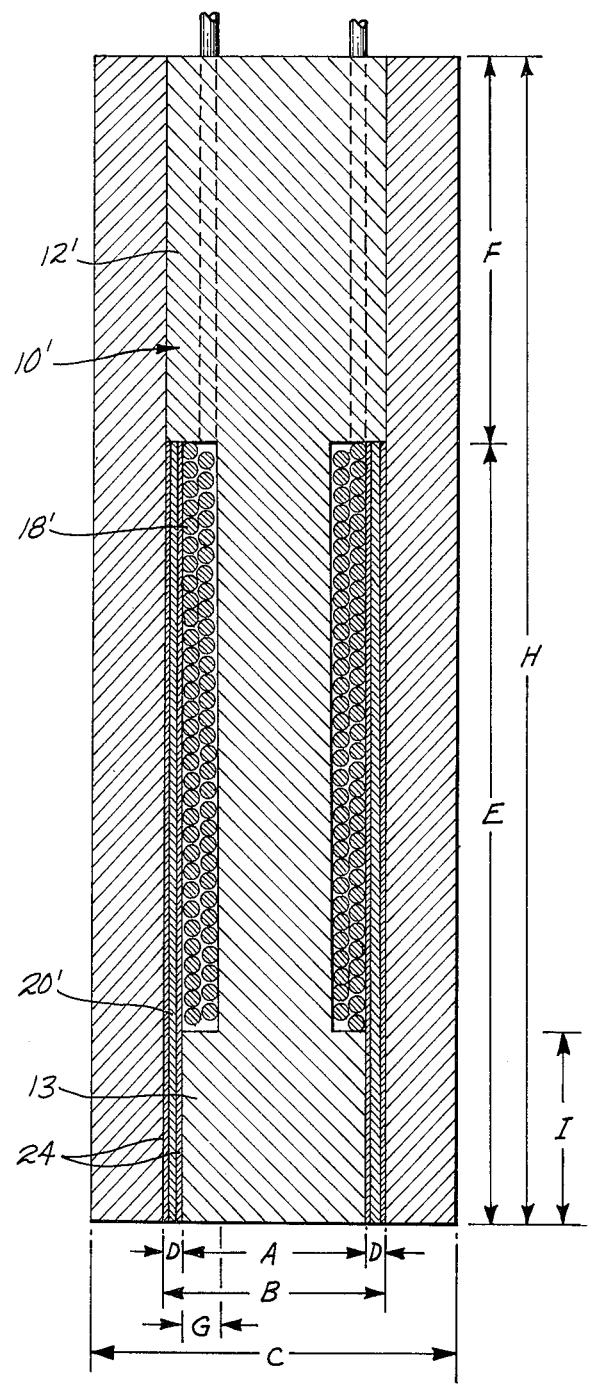
FIG. 7 is a view similar to FIG. 3, but of a modified embodiment of the invention.

The embodiment shown by FIG. 7 is similar to the embodiment shown by FIGS. 3 – 6 except that the gap size may be considerably smaller since it is not dependent upon the restrictive space requirements of the coil 18'. In the embodiment of FIGS. 3 – 6 a single winding coil 18 is usually employed and the gap D, G must be large enough to accommodate both the shielding material 20 and the coil material 18. In the embodiment shown by FIG. 7 the minimum gap D is limited only by the thickness required to obtain high reluctance through the split annular sheet 20'. Either a single or multiple wrap coil 18' can be employed and it is located within a recess formed between the two end portions 12' and 13 of the core 10'.

Example geometries of the controlled reluctance eddy-current generator shown by FIG. 7 are as follows:

| | |
|---|---|
| A | 0.028" – 0.024" diam. |
| B | 0.029" – 0.035" diam. |
| C | 0.048" diam. |
| D | 0.005" – 0.002" thick annular sheet |
| E | 0.100" |
| F | 0.050" |
| G | no restriction |
| H | 0.150" |
| I | No restriction |

With respect to both of the above-described embodiments it may be said that the probe PR comprises a main body of low reluctance magnetic material which defines an annular, axially elongated, internal chamber that is bounded on all sides by the low reluctance magnetic material except for in the region of an annular gap in said body which extends axially outwardly from said chamber to a break in an external surface of said body. The concentric coil and sleeve of high reluctance material are located within said chamber and high reluctance material extends through the gap and terminates substantially even with surface portions of said body which immediately bound both sides of the surface break, thus forming an annular test gap region which in use is positioned contiguous a material to be tested (as shown by FIG. 6).

The following description relates to additional embodiments of my eddy-current generator probe which are basically characterized in the same way.

Figure 8:
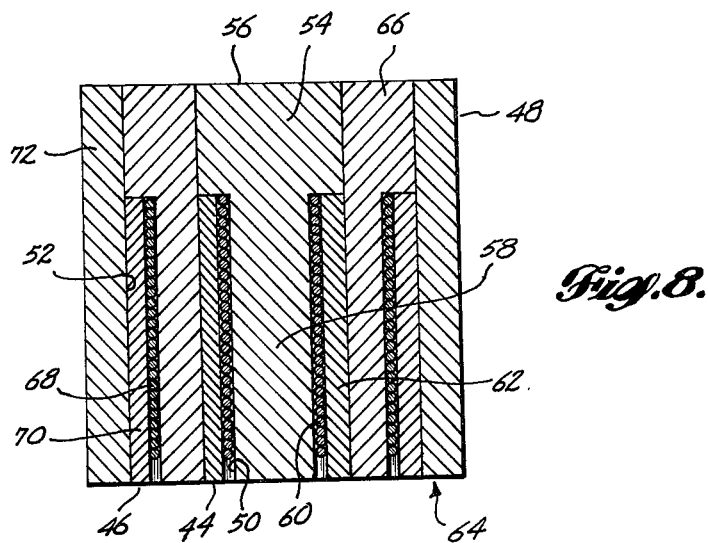
FIG. 8 is a view like FIGS. 3 and 7 of a second embodiment of the invention, characterized by a pair of concentric test gaps.

Referring to FIG. 8, this embodiment comprises a pair of concentric test gaps 44, 46. The probe body 48 defines a first annular chamber 50 and a second annular chamber 52 surrounding it. Again, for convenience of manufacture, the body 48 is shown to be manufactured in several parts. A first part 54 has an enlarged upper end (as shown) portion 56 and a longer, reduced diameter portion 58 which forms a core for a first exciting coil 60. A first sleeve of high reluctance material 62 is shown to concentrically surround the first coil 60, with both of them being located within the first chamber 50. As in the above described embodiments, the gap extends axially from chamber 50 and breaks the lower (as illustrated) end surface 64 of probe body 48. The high reluctance material extends axially endwise outwardly and itself terminates as a part of the surface 64. A tubular low reluctance second part 66 of probe body 48 surrounds the first part 54, the chamber 50, and the coil 60 and the high reluctance sleeve 62 therein. Part 66 is recessed to help form the second annular chamber 52 and the inner part thereof bounding such chamber 52 functions as a core for a second exciting coil 68. A second sleeve 70 of high reluctance material concentrically bounds the coil 68 and extends endwise through the gap to the surface break at end surface 64. A third portion 72 of the low reluctance body surrounds and encases the part 54, 66, the coils 60, 68 and the high reluctance sleeve 62, 70, and helps define the outer annular chamber 52.

In operation, the two coils 62, 68 are operated at the same or different frequencies. The differential readings that are obtained from each coil may be used for several purposes. For example, they can be used to differentiate lift-off signals from cracks. Also, surface cracks and coating thickness can be measured at one time.

Figures 9, 10, 11:
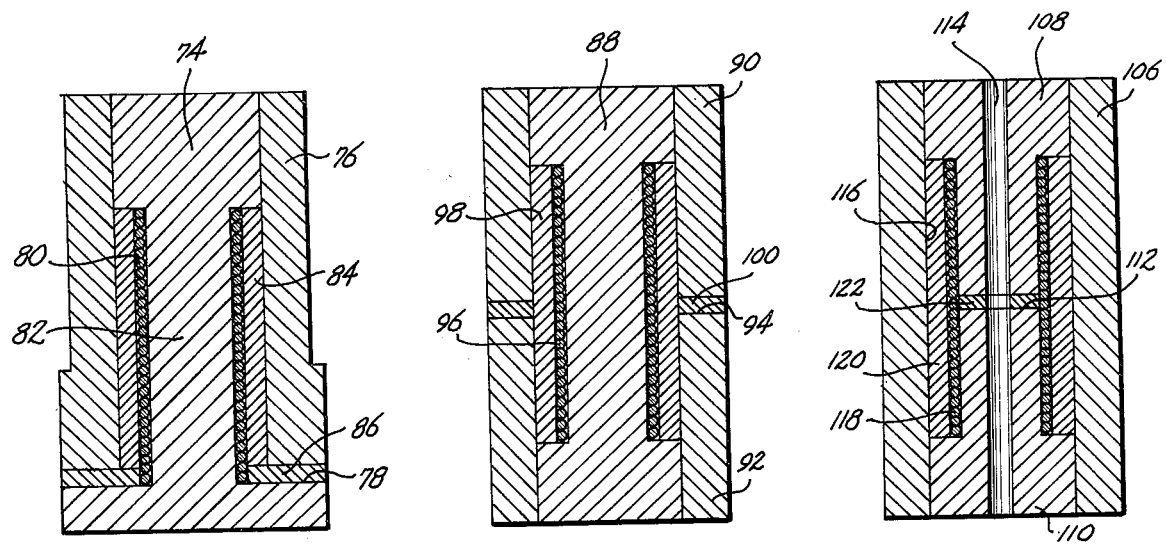
FIG. 9 is also a view like FIGS. 3, 7, and 8, but of yet another embodiment of the invention, characterized by a radial annular test gap.
FIG. 10 is yet another view like FIGS. 3, 7, 8, and 9, of yet another embodiment of the invention, also characterized by a radial test gap.
FIG. 11 is still another longitudinal sectional view of still another embodiment of the invention, also characterized by a radial test gap.

FIGS. 9 – 11 show additional forms which are identical in principle to the above forms. However, in each of these embodiments the gaps extend radially and the surface breaks and test gaps extend circumferentially about a peripheral or side wall portion of the probe.

The probe shown by FIG. 9 includes an inner portion 74, an outer portion 76, together defining a radial gap at 78. As before, an exciting coil concentrically surrounds a core portion 82 of the inner part 74 and a sleeve of high reluctance material 84 concentrically surrounds coil 80. Also, high reluctance material 86 extends radially outwardly through gap 78 and terminates at an outer surface break which extends circumferentially about the probe. This embodiment would be suitable for testing, for example, tubing from the interior surface or for inspecting fastener holes.

FIG. 10 discloses a quite similar structure, except that the radial gap is formed intermediate the ends of the coil. This embodiment comprises an inner spool shaped piece of low reluctance material surrounded by a pair of annular low reluctance members 90, 92 which are axially spaced apart at their inner ends to form a gap 94. The exciting coil 96 surrounds the reduced diameter portion of part 88 at a sleeve of high reluctance material 98 surrounds the coil 96. High reluctance material 100 is disclosed within gap 94 and extends from high reluctance material 98 out to the circumferentially extending break in the outer peripheral surface of the body. FIG. 12 shows that the high reluctance material 98 may be tubular in form with a split or interruption 102 provided to prevent current flow circumferentially around and through the member 98. Similarly, (FIG. 13) the high reluctance material 100 within gap 94 may include a break 104 which when the parts are assembled is aligned with the break 102. The embodiments disclosed by FIGS. 9 and 10 are designed for movement into or relatively through a tubular member, for testing internal surface conditions of the tubular member.

The embodiment shown by FIG. 11 may be referred to as an outside-in version of the embodiment shown by FIG. 10. Its main body of low reluctance material comprises a one piece outer member 106 which surrounds a two piece inner portion. The two inner parts 108, 110 together have a spool like configuration, such as inner part 88 of FIG. 10, except that a radial gap 112 is defined axially between two inner end surfaces thereof. Also, a central passageway 114 is formed axially through the members 108, 110. As in the other embodiments, an annular chamber 116 is formed by and between the body parts 106, 108, 110. An exciting coil 118 and a concentric sleeve 120 of high reluctance material are located within the chamber 116. A washer-like high reluctance member 122 is located within the gap 112. The side walls of the hole through member 122 is substantially even with the side wall of the central opening 114. In this embodiment the material to be tested is moved into and/or relatively through the central passageway 114, and is especially suitable for inspecting wire, rod, or tubing from the exterior surface.

It should be apparent that the various embodiments shown and described are only exemplatory and that various other modifications can be made in construction and arrangement of the probe while the scope of the invention, described in the appended claims.

What is claimed is:

1. An eddy-current generator type test probe for material testing use, said probe comprising:
    a main body of low reluctance magnetic material defining an annular, internal chamber that is bounded on all sides by the low reluctance magnetic material except for in the region of an annular gap in said body which extends from said chamber to break an externally connected surface of said body,
    an axially wound exciting coil of electrically conductive wire within said annular chamber, said coil being the only coil within said annular chamber and including terminal means for use in connecting said coil to alternating current means for operating said coil at a suitable frequency for the particular material testing to be done,
    a sleeve of high reluctance material within said chamber, concentric with said coil and extending lengthwise of the body adjacent said coil for the full length of said coil, and high reluctance material extending through said gap in the low reluctance material from said concentric coil and sleeve of high reluctance material, terminating substantially even with surface portions of said body which immediately bound both sides of said surface break, and forming therewith an annular test gap region which in use is positioned contiguous a material to be tested,
    said low reluctance material including a core portion, said concentric coil and sleeve of high reluctance material immediately surrounding said core portion, and said low reluctance material including a surrounding portion which immediately surrounds said concentric coil and sleeve of high reluctance material, and
    said high reluctance material being selected to have a reluctance that is much higher than the reluctance of the material to be tested and being a material which at the operating frequency of the coil during material testing use has an electromagnetic skin depth which is substantially less than the thickness of said high reluctance material, so that said high reluctance material influences substantially all of the magnetic flux which is generated by the coil to flow outwardly of said body, across said gap and through the material being tested, resulting in the total reluctance of the magnetic circuit being concentrated within the material being tested.

2. An eddy-current generator probe according to claim 1, wherein said annular gap in said body of low reluctance material extends axially from said internal chamber and breaks an end surface portion of said probe.

3. An eddy-current generator probe according to claim 2, comprising a second annular, internal chamber formed in said main body of low reluctance magnetic material which is bounded on all sides by low reluctance magnetic material except for in the region of a second annular gap in said body which extends axially from said second internal chamber and also breaks said end portion of said probe, said second chamber being concentric with said first chamber, an axially wound second exciting coil of electrically conductive wire within said second chamber, said second coil being the only coil within said second chamber and also including terminal means for use in connecting said second coil to an alternating current means adopted to operate it, a second sleeve of high reluctance material, as defined, within said second chamber, concentric with said second coil and extending lengthwise of the body adjacent said second coil for the full length of said second coil, and extending through said second axial gap in the low reluctance material and terminates substantially even with end surface portions of said body which immediately bound both sides of said second surface break, and forming therewith a second annular test gap region which in use is positioned contiguous a material to be tested, said low reluctance material also including a portion which is a core portion to said second coil, and said concentric second coil and second sleeve of high reluctance material immediately surrounds said second core portion, and said low reluctance material includes a surrounding portion which immediately surrounds said concentric second coil and said second sleeve of high reluctance material.

4. An eddy-current generator probe according to claim 1, wherein said annular gap extends radially outwardly and breaks an outer peripheral surface of said body.

5. An eddy-current generator according to claim 1, wherein said main body of low reluctance magnetic material includes a central passageway extending axially therethrough concentric with said internal chamber, and wherein the annular gap extends from said internal chamber radially toward said central passageway and breaks a side wall surface portion of said passageway.

6. Eddy-current generator type apparatus for material testing use, comprising:
  a probe having a main body of low reluctance magnetic material defining an annular, internal chamber that is bounded on all sides by the low reluctance magnetic material except for in the region of an annular gap in said body which extends from said chamber to break an externally connected surface of said body,
  an axially wound exciting coil of electrically conductive wire within said annular chamber, said coil being the only coil within said annular chamber and including terminal means,
  a sleeve of high reluctance material within said chamber, concentric with said coil and extending lengthwise of the body adjacent said coil for the full length of said coil, and high reluctance material extending through said gap in the low reluctance material from said concentric coil and sleeve of high reluctance material, terminating substantially even with surface portions of said body which immediately bound both sides of said surface break, and forming therewith an annular test gap region which in use is positioned contiguous a material to be tested,
  said low reluctance material including a core portion, said concentric coil and sleeve of high reluctance material immediately surrounding said core portion, and said low reluctance material including a surrounding portion which immediately surrounds said concentric coil and sleeve of high reluctance material,
  alternating current means connected to the terminal means of said coil, for operating said coil at a suitable frequency for the particular material testing to be done, and
  said high reluctance material within said probe being selected to have a reluctance that is much higher than the reluctance of the material to be tested and being a material which at the operating frequency of the coil during material testing use has an electromagnetic skin depth which is substantially less than the thickness of said high reluctance material, so that said high reluctance material influences substantially all of the magnetic flux which is generated by the coil to flow outwardly of said body, across said gap and through the material being tested, resulting in the total reluctance of the magnetic circuit being concentrated within the material being tested.

7. Eddy-current generator apparatus according to claim 6, wherein said annular gap in said body of low reluctance material extends axially from said internal chamber and breaks an end surface portion of said probe.

8. Eddy-current generator apparatus according to claim 7, comprising a second annular, internal chamber formed in said main body of low reluctance magnetic material which is bounded on all sides by low reluctance magnetic material except for in the region of a second annular gap in said body which extends axially from said second internal chamber and also breaks said end portion of said probe, said second chamber being concentric with said first chamber, an axially wound second exciting coil of electrically conductive wire within said second chamber and also including terminal means for use in connecting said second coil to an alternating current means adapted to operate it, a second sleeve of high reluctance material, as defined, within said second chamber, concentric with said second coil and extending lengthwise of the body adjacent said second coil for the full length of said second coil, and extending through said second axial gap in the low reluctance material and terminates substantially even with end surface portions of said body which immediately bound both sides of said second surface break, and forming therewith a second annular test gap region which in use is positioned contiguous a material to be tested, said low reluctance material also including a portion which is a core portion to said second coil, and said concentric second coil and second sleeve of high reluctance material immediately surrounds said second core portion, and said low reluctance material includes a surrounding portion which immediately surrounds said concentric second coil and said second sleeve of high reluctance material.

9. Eddy-current generator apparatus according to claim 6, wherein said annular gap extends radially outwardly and breaks an outer peripheral surface of said body.

10. Eddy-current generator apparatus according to claim 6, wherein said main body of low reluctance magnetic material includes a central passageway extending axially therethrough concentric with said internal chamber, and wherein the annular gap extends from said internal chamber radially toward said central passageway and breaks a side wall surface portion of said passageway.

11. An eddy-current generator for material testing use, comprising:
  an elongated composite probe having a probe end which in use is positioned on a surface of a material being tested, and an opposite end, said probe comprising:
    an exciting coil of electrically conductive wire having a first end directed towards the material being tested and a second opposite end,
    low reluctance magnetic material establishing a low reluctance magnetic path within said probe, comprising a core portion about which said coil extends and including an end surface at said probe end, an outer portion surrounding said coil in a spaced relationship with said core portion and also including an end surface at said probe end, and an end portion which is magnetically integral with both said core portion and said outer portion and which extends endwise therefrom towards said probe's opposite end, said magnetic path of magnetic material extending uninterrupted from said core portion through said end part into said outer portion, only one electrically conductive sleeve of high reluctance material concentric with said coil and extending lengthwise of said probe adjacent said coil from the second end of said coil only to the probe end and including an end surface at said probe end, said concentric coil and sleeve of high reluctance material immediately surrounding said core portion, said coil being the only coil in said probe, said outer portion of said low reluctance material immediately surrounding said concentric coil and sleeve of high reluctance material, said outer portion of said low reluctance material and said core portion of said low reluctance material together defining a gap at said probe end, said high reluctance material occupying said gap, and said end surfaces of said high and low reluctance materials being substantially even with each other at said probe end, said high reluctance material being selected to have a reluctance that is much higher than the reluctance of the material to be tested and being a material which at the operating frequency of the coil has an electromagnetic skin depth which is substantially less than the thickness of said high reluctance material, so that said high reluctance material influences substantially all of the magnetic flux which is generated by the coil to flow through the material being tested, resulting in the total reluctance of the magnetic circuit being concentrated within the material being tested.

12. An eddy-current generator according to claim 11, wherein the high reluctance material is a NiFe alloy.

13. An eddy-current generator according to claim 11, wherein said coil is wrapped about said core portion of said low reluctance material and said high reluctance material is of sheet form, is insulated on both of its sides, and is wrapped around said coil and partially around itself, so that insulated portions thereof overlap and prevent current flow through said high reluctance material.

* * * * *

UNITED STATES PATENT OFFICE
CERTIFICATE OF CORRECTION

Patent No. 4,088,953  Dated May 9, 1978

Inventor(s) Suren Sarian

It is certified that error appears in the above-identified patent and that said Letters Patent are hereby corrected as shown below:

Column 5, line 63, the equation should appear as follows:

$$\frac{\Delta L}{L} \cong - \frac{2R_o}{(24R_o)(26R_o)} \cdot \Delta R_m \cong - 0.003 \frac{\Delta R_m}{R_o}$$

Column 7, line 3 "othermaterial" should be -- other material -- .

Column 9, line 45, "C 0.48" diam." should be -- C 0.048" diam. -- .

Signed and Sealed this

Tenth Day of October 1978

|SEAL|

Attest:

RUTH C. MASON
*Attesting Officer*

DONALD W. BANNER
*Commissioner of Patents and Trademarks*